United States Patent [19]

Boyer

[11] 4,042,696

[45] Aug. 16, 1977

[54] INSECTICIDAL SULFONIUM SALTS

[75] Inventor: Alvin Clifford Boyer, Modesto, Calif.

[73] Assignee: Shell Oil Company, Houston, Tex.

[21] Appl. No.: 659,886

[22] Filed: Feb. 20, 1976

Related U.S. Application Data

[63] Continuation-in-part of Ser. No. 582,577, June 2, 1975, abandoned.

[51] Int. Cl.² .................. A01N 9/22; C07D 239/02
[52] U.S. Cl. ........................... 424/251; 424/273 R; 260/251 R; 548/342
[58] Field of Search .......................... 424/273, 251; 260/309.7, 251 R

[56] References Cited

U.S. PATENT DOCUMENTS

| | | | |
|---|---|---|---|
| 3,152,108 | 10/1964 | Taber | 260/309.7 |
| 3,728,355 | 4/1973 | D'Amico et al. | 260/309.7 |

OTHER PUBLICATIONS

Chemical Abstracts, vol. 71 (1969), p. 7552F.

*Primary Examiner*—V. D. Turner

[57] ABSTRACT

Novel insecticidal sulfonium salts of 2-(alkylthio)ethyl esters of α-nitro-α-(1-alkyl-1,3-diazacycloalk-2-ylidene)acetic acids.

5 Claims, No Drawings

INSECTICIDAL SULFONIUM SALTS

This application is a continuation-in-part of copending application Ser. No. 582,577, filed June 2, 1975, now abandoned.

DESCRIPTION OF THE INVENTION

It has been found that useful insecticidal activity is possessed by certain sulfonium salts of certain esters of α-nitro-α-(1-alkyl-1,3-diazacycloalk-2-ylidene)acetic acids, of the formula:

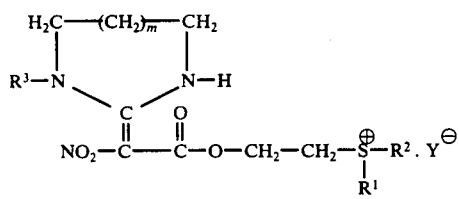

(I)

These salts are resonance hybrids, and may exist in the tautomeric enol forms, and all may exist as geometric isomers.

In this specification, for the sake of simplicity, these salts will be defined in terms of Formula (I). The definition is intended to include all of the contributors to the resonance hybrid, the geometric isomers and the enol form, as well as mixtures thereof.

In these salts, $m$ is 0 or 1, $R^1$ is alkyl of from 1 to 3 carbon atoms, $R^2$ is alkyl of from 1 to 10 carbon atoms, $R^3$ is alkyl or cyanoalkyl of 1 to 3 carbon atoms, or is allyl, 3-chloroallyl or 2-propynyl and Y is an anion.

Because of their insecticidal activity characteristics, a preferred sub-genus of the genus of the invention consists of those compounds of the general formula wherein $m$ is 1, $R^1$ and $R^3$ each is methyl, $R^2$ is alkyl of one to six carbon atoms and Y is chloride, bromide or iodide.

For illustration, preparation of typical species of the genus is described in the examples included hereinafter. Other typical, illustrative species of this genus include those wherein the symbols represent the following moieties, this manner of naming these species being accurate, yet pointing out the differences between the different species more clearly than if the entire, complicated name of each species were to be given:

| $R^1$ = methyl, $R^2$ = methyl, $R^3$ = | 3-chloroalkyl |
|---|---|
| | 2-propynyl |
| | cyanomethyl |

The salts of this invention are readily prepared by treating the corresponding 2-($R^2$-thio)ethyl esters with the appropriate compound $R^1$-Y, in a suitable solvent, at room temperature or moderately above — for example, up to 50° C. The suitable $R^1$-Y compounds include those wherein Y is chlorine, bromine or iodine, alkyl sulfate (alkyl-$SO_4^-$), or fluoborate ($BF_4^-$).

The precursor 2-($R^2$-thio)ethyl esters can be prepared by the base-promoted transesterification of an alkyl ester

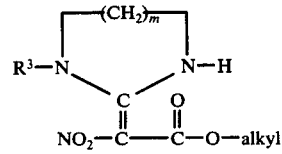

such as the methyl or ethyl ester, by treating the alkyl ester with at least two equivalents of an alkali metal alcoholate of the appropriate 2-($R^2$-thio)ethyl alcohol, in a solvent such as dimethylformamide. This may be done by treating the alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at or somewhat above room temperature. Recovery of the product is most effectively attained in most cases by quenching the final reaction mixture in water, treating the aqueous mixture with a suitable solvent such as ether to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ethyl ether.

The preparation of the alkyl ester precursors can be effected as illustrated in Examples 1-3 hereinafter, employing a 1-alkyl-imidazolidine-2-thione, (McKay et al., J. Org. Chem., 22, 1581 (1957) or a tetrahydro-1-($R^3$)-2-(IH)pyrimidinethione (Gilli, et al., Ric. Sci 1968, 38 (9),840-1; C.A., 71, 7552f (1969)).

The procedures for preparing compounds of this invention are illustrated in the following example of the preparation of particular species of such compounds. In all cases the identity of the precursor (s) was established and the identity of the final product was confirmed, by appropriate analyses.

EXAMPLE 1

Dimethyl(2-((1-Methyl-2-Imidazolidinylidene)Nitroacetyloxy)Ethyl)-Sulfonium Iodide(1)

360 g of dimethyl sulfate was added dropwise to a stirred and refluxing suspension of 332 g of 1-methylimidazolidine-2-thione in 900 ml of hexane. After 2 hours further stirring at the same temperature, the mixture was cooled and treated with 114 g of sodium hydroxide in 320 ml of water. The hexane layer was separated and dried ($MgSO_4$). The aqueous layer was extracted with methylene chloride and the extract was dried ($MgSO_4$). The solvents were evaporated under reduced pressure and the combined residues were distilled to give 1-methyl-2-(methylthio)-2-imidazoline (1A) as a colorless liquid, b.p.: 50°–52° at 0.02 Torr.

19.5 g of 1A, 17.8 g of methyl nitroacetate and a small amount of zinc chloride were mixed and the mixture heated to 100°–105°. After 30 minutes, the solid reaction mixture was washed with ether, then with hot methanol. The mixture then was filtered to give the methyl ester of (1-methyl-2-imidazolidinylidene)nitroacetic acid (1B) as a tan solid, m.p.: 209°–210°.

4.02 g of 1B, 35 g of 2-(methylthio)ethanol, 2.2 g of 45% sodium hydride in mineral oil, and 25 ml of dry dimethylformamide were mixed and the mixture was stirred overnight at room temperature. The mixture then was poured into water and extracted with methylene chloride. 5 ml of acetic acid was added to the aqueous layer, which was extracted with methylene chloride. The latter extract was dried (MgSO$_4$) and the solvent was evaporated to give a light yellow oil, which was triturated with a mixture of petroleum ether and ethyl acetate. Filtration gave a white powder, which was recrystallized from petroleum ether/methylene chloride to give the 2-(methylthio)ethyl ester of (1-methyl-2-imidazolidinylidene)nitroacetic acid (1C).

1.31 g of 1C was dissolved in 10 ml of methylene chloride and treated with methyl iodide (10 ml). The mixture was refluxed for 4 hours, then filtered. The resulting crystals were washed with acetone and dried under reduced pressure, to give 1, as light tan crystals, m.p.: 154°–155° (with gas evolution).

EXAMPLE 2

(2-((Hexahydro-1-Methyl)-2-Pyrimidinylidene)Nitroacetoxy)Ethyl)Dimethylsulfonium Iodide (2)

2 was prepared as a light brown solid, m.p.: 149–151 (gas evolution), from hexahydro-1-methyl-2-pyrimidinethione (Gili et al., supra) and ethyl nitroacetate, by the procedures described in Example 1.

EXAMPLE 3

Dimethyl((2-(1-Allyl-2-Imidazolidinylidene)Nitroacetyloxy)Ethyl)Sulfonium Iodide (3)

3 was prepared as white crystals, m.p.: 137–138 (gas evolution) from 1-allyl-2-imidazolidinethione (German Offenlegungschrift No. 2,349,527) and ethyl nitroacetate, by the procedures described in Example 1.

In Examples 2 and 3, the preparation of the alkyl ester intermediate was carried out in isopropyl alcohol, to moderate the reaction, and no zinc chloride catalyst was used.

The salts of this invention exhibit useful insecticidal activity, being of particular interest for control of the larval "caterpillar" or "worm" forms of lepidopterous insects of the genus Heliothis, such as *H. zea* (corn earworm, cotton bollworm, tomato fruitworm), *H. virescens* (tobacco budworm); the genus Agrotis, such as *A. ipsilon* (black cutworm); the genus Trichoplusia, such as *T. Ni* (cabbage looper), and the genus Spodoptera, such as *S. littoralis* (Egyptian cotton leafworm).

The activity of Compounds 1-3 with respect to insects was determined by using standardized test methods to establish the LC$_{50}$ dosage (in milligrams of test compound per 100 milliliters of solvent or liquid carrier required in the solution of suspension of test compound used) that was required to kill 50% of the test insects. The test insects were the housefly, corn earworm, pea aphid and 2-spotted spider mite. Activity with respect to mosquito larvae was determined by placing the larvae in water containing the test compound.

Compounds 1 and 2 were found to be inactive with respect to the housefly and mites, slightly active with respect to the aphids and mosquito larvae, and moderately to very active with respect to the corn earworms. Compound 3 had a similar spectrum; except that it was inactive with respect to the aphids. In the course of the tests it was noted that compound 1 acted very quickly on the corn earworm.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the salts of this invention and liquids in which the toxicant is insoluble or only slightly soluble.

Examples of such solvents and liquid carriers generally are water, alcohols, for example, isopropyl alcohol; ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils; chlorinated hydrocarbons, such as carbon tetrachloride, perchlorethylene, trichloroethane; including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10%w of active ingredient. Granules may be manufactured by agglomeration or impregnation techniques. Generally, granules will contain ½-25%w active ingredient and 0-10%w of additives such as stabilizers, slow release modifiers and binding agents. Emulsifiable concentrates usually contain, in addition to the solvent, and when necessary, co-solvent, 10-50%w/v active ingredient, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w active ingredient, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the active ingredient is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of the active ingredient at the locus being within the skill of those versed in the art. In general, however, the effective dosage of salts of this invention at the locus to be protected — i.e. the dosage to which the insect contacts — is of the order of 0.001 to 0.5% based on the total weight of the formulation, though under some circumstances the effective concentration will be as little as 0.001% or as much as 2%, on the same basis.

What is claimed is:

1. A sulfonium salt of the formula:

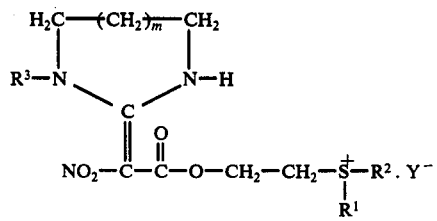

wherein $m$ is 0 or 1, $R^1$ is alkyl of from 1 to 3 carbon atoms, $R^2$ is alkyl of from 1 to 10 carbon atoms, $R^3$ is alkyl or cyanoalkyl of from 1 to 3 carbon atoms, or is allyl, 3-chloroallyl or 2-propynyl and Y is chloride, bromide or iodide.

2. A salt according to claim 1 wherein $R^1$ and $R^3$ each is methyl.

3. A salt according to claim 2 wherein $R^2$ is methyl.

4. An insecticidal composition adapted to controlling insects of the genus Heliothis comprising an insecticidal amount of a salt of claim 1 together with an insecticidal adjuvant therefor.

5. A method for killing insects of the genus Heliothis which comprises contacting the insects with a lethal amount of a salt of claim 1.

* * * * *